US010398894B2

(12) United States Patent
Johansson et al.

(10) Patent No.: US 10,398,894 B2
(45) Date of Patent: Sep. 3, 2019

(54) ORAL DEVICE WITH ACTIVATING ELEMENT

(71) Applicant: COLGATE-PALMOLIVE COMPANY, New York, NY (US)

(72) Inventors: Patrik Johansson, Hoboken, NJ (US); Evaristo Delgado, Fanwood, NJ (US); Daniel Wainless, New Brunswick, NJ (US)

(73) Assignee: Colgate-Palmolive Company, New York, NY (US)

( * ) Notice: Subject to any disclaimer, the term of this patent is extended or adjusted under 35 U.S.C. 154(b) by 1 day.

(21) Appl. No.: 15/390,824

(22) Filed: Dec. 27, 2016

(65) Prior Publication Data

US 2018/0178005 A1    Jun. 28, 2018

(51) Int. Cl.
| | | |
|---|---|---|
| *A61C 1/05* | (2006.01) | |
| *A61N 1/30* | (2006.01) | |
| *A61N 1/05* | (2006.01) | |
| *A61C 19/06* | (2006.01) | |

(52) U.S. Cl.
CPC ............ *A61N 1/306* (2013.01); *A61C 19/063* (2013.01); *A61C 19/066* (2013.01); *A61N 1/0548* (2013.01)

(58) Field of Classification Search
CPC .... A61N 1/306; A61N 1/0548; A61C 19/063; A61C 19/066
See application file for complete search history.

(56) References Cited

U.S. PATENT DOCUMENTS

| | | | |
|---|---|---|---|
| 3,118,450 A | | 1/1964 | Freeman et al. |
| 3,502,076 A | | 3/1970 | Bertolini |
| 5,316,473 A | * | 5/1994 | Hare ................... A61C 19/004 433/215 |
| 5,924,863 A | * | 7/1999 | Jacobs ................. A61C 9/0006 433/37 |
| 7,775,795 B2 | | 8/2010 | Khawaled et al. |
| 9,168,370 B2 | | 10/2015 | Nemeh et al. |
| 9,308,064 B2 | | 4/2016 | Binner et al. |
| 9,913,992 B2 | * | 3/2018 | Demarest ............. A61N 5/0603 |
| 9,968,777 B1 | * | 5/2018 | Demarest ............... A61N 1/306 |
| 2006/0127837 A1 | * | 6/2006 | Nguyen ............... A61C 19/063 433/29 |
| 2007/0292819 A1 | * | 12/2007 | Scarberry .............. A61F 5/566 433/140 |
| 2008/0003540 A1 | * | 1/2008 | Khawaled ........... A61C 19/066 433/215 |

(Continued)

FOREIGN PATENT DOCUMENTS

| | | |
|---|---|---|
| DE | 2740188 A1 | 3/1979 |
| EP | 1525857 | 2/2007 |
| WO | 2008/001388 | 1/2008 |

OTHER PUBLICATIONS

International Search Report and Written Opinion of the International Searching Authority in International Application No. PCT/US2017/067115, dated Aug. 7, 2018.

*Primary Examiner* — Nicholas D Lucchesi

(57) ABSTRACT

An oral care implement herein may be embodied as an oral device for placement in the oral cavity. The device may include an insert configured for placement in the oral cavity in contact with a wearer's teeth and an activating member configured for placement in the oral cavity and selectively attachable to the insert.

19 Claims, 8 Drawing Sheets

(56) References Cited

U.S. PATENT DOCUMENTS

| | | | |
|---|---|---|---|
| 2008/0008978 A1* | 1/2008 | Conrad | A61C 19/06 433/32 |
| 2008/0233541 A1* | 9/2008 | De Vreese | A61C 19/003 433/216 |
| 2009/0017422 A1* | 1/2009 | Creamer | A61C 19/06 433/215 |
| 2012/0156648 A1 | 6/2012 | Kaufman et al. | |
| 2015/0044628 A1* | 2/2015 | Flyash | A61C 19/066 433/27 |
| 2015/0140502 A1* | 5/2015 | Brawn | A61C 7/08 433/24 |
| 2018/0206957 A1* | 7/2018 | Ruth | A61C 19/003 |

* cited by examiner

ORAL DEVICE WITH ACTIVATING ELEMENT

BACKGROUND

Various products and processes have been developed to improve and maintain oral health. For example, formulations such as mouthwashes, creams, pastes, salves, and the like, are known for reducing bacteria in the mouth and/or for treating other oral conditions. Conventionally, the formulations are applied to the teeth, gums and/or other areas of the oral cavity by rinsing, brushing, or otherwise. In some instances, substances are applied to the teeth or oral cavity and activated, e.g., using electrical fields or irradiation, to provide oral benefits. However, there is a need in the art for improved implements and methods for treating the oral cavity.

Accordingly, there is a need in the art for effective oral care devices. This disclosure is directed at overcoming one or more problems set forth above and/or other problems of the prior art.

BRIEF SUMMARY

This application describes improved oral care implements and methods for treating the oral cavity. In some embodiments, an oral care implement herein may be embodied as an oral device for placement in the oral cavity. The device may include an insert configured for placement in the oral cavity in contact with a wearer's teeth and an activating member configured for placement in the oral cavity and selectively attachable to the insert. The insert carries an activating agent and may be configured to place the activating agent in intimate contact with the wearer's teeth. The activating member includes a power source (e.g., a battery) for powering an activating element. In some example embodiments, the activating element may include electrodes for, along with the activating agent, providing an electrochemical benefit to the wearer's teeth. In other embodiments, the activating element may be a light source positioned to irradiate the wearer's teeth.

In one example implementation, an oral device according to this disclosure includes an insert configured for placement in an oral cavity in contact with teeth in the oral cavity and an activating member configured for placement in the oral cavity. The insert may include a facial portion comprising a first surface configured for placement proximate a facial surface of the teeth; a lingual portion comprising a second surface spaced from the first surface and configured for placement proximate a lingual surface of the teeth; a base connecting the facial portion and the lingual portion, the base, the first surface, and the second surface forming a channel for receiving the teeth; a first electrode arranged proximate the first surface, in proximity to the facial surface of the teeth; a second electrode spaced from the first electrode; and at least one first electrical connector electrically connected to at least one of the first electrode or the second electrode. The activating member may include: a housing configured to be completely received in the oral cavity; a power source disposed in the housing; and at least one second electrical connector electrically connected to the power source, the at least one second electrical connector being connectible to the at least one first electrical connector to supply power from the power source in the activating member to the first electrode and the second electrode in the insert.

In another implementation, in the oral device according to the preceding paragraph(s), the housing may include a housing base, an arcuate housing facial wall extending from a top surface of the housing base, and an arcuate housing lingual wall extending from the top surface and spaced from the lingual wall.

In another implementation, in the oral device according to the preceding paragraph(s), a third surface of the facial wall, a fourth surface of the lingual wall facing the third surface, and the top surface of the base may form at least part of a receptacle configured to receive the insert.

In another implementation, in the oral device according to the preceding paragraph(s), a spacing between the third surface and the fourth surface may provide an interference fit between the activating member and an outer surface of the insert.

In another implementation, in the oral device according to the preceding paragraph(s), a spacing distance between the third surface and the fourth surface may vary at discrete distances from the top surface of the housing base.

In another implementation, in the oral device according to the preceding paragraph(s), the spacing may be smaller at a first location farther from the top surface than at a second location closer to the top surface.

In another implementation, in the oral device according to the preceding paragraph(s), the facial portion may include a first facial portion and the lingual portion may include a first lingual portion, and the channel may be configured for receiving maxillar teeth of the teeth, the insert may further include a second facial portion extending, relative to the base, in a substantially opposite direction as the first facial portion, the second facial portion may include a third surface configured for placement proximate a facial surface of mandibular teeth in the oral cavity; and a second lingual portion extending, relative to the base, in a substantially opposite direction as the first lingual portion, the second lingual portion comprising a fourth surface configured for placement proximate a lingual surface of the mandibular teeth, the third surface, the fourth surface, and the base may form at least a portion of a second channel for receiving the mandibular teeth.

In another implementation, in the oral device according to the preceding paragraph(s), the housing may include an arcuate housing facial wall configured to contact at least one of an outer surface of the first facial portion or an outer surface of the second facial portion.

In another implementation, in the oral device according to the preceding paragraph(s), one of the activating member or the insert may include a protrusion and the other of the activating member or the insert may include a receptacle for releasably receiving the protrusion.

In another implementation, in the oral device according to the preceding paragraph(s), the first electrical connector may be disposed on the protrusion or in the receptacle and the second electrical connector may be the other of disposed on the protrusion or in the receptacle.

In other implementations of this disclosure, an oral device may include an insert configured for placement in an oral cavity and an activating member configured for placement in the oral cavity and releasably retained in operable communication with the insert. The insert may include a facial portion comprising a first surface configured for placement proximate a facial surface of the teeth, a lingual portion comprising a second surface spaced from the first surface and configured for placement proximate a lingual surface of the teeth, a base connecting the facial portion and the lingual portion, the base, the first surface, and the second surface forming a channel for receiving the teeth, and an active agent disposed in the channel. The activating member may include a power source for powering an electronic element that cooperates with the active agent to apply a benefit to the teeth.

In another implementation, in the oral device according to the preceding paragraph(s), the insert may further include a first electrode disposed proximate the first surface and a second electrode disposed proximate at least one of the second surface or the base.

In another implementation, the oral device according to the preceding paragraph(s), may further include a first electrical contact on the insert and a second electrical contact on the activating member in electrical communication with the power source, wherein the first electrical contact and the second electrical contact may be electrically connected when the activating member is placed in operable communication with the inert.

In another implementation, in the oral device according to the preceding paragraph(s), the emerging member may include a U-shaped receptacle configured to receive the insert.

In another implementation, in the oral device according to the preceding paragraph(s), the insert may include a first electrical contact disposed on an external surface of the insert, opposite the channel, the activating member may include a second electrical contact on an interior surface of the receptacle, and positioning of the insert in the receptacle may place the first electrical contact in contact with the second electrical contact.

In another implementation, the oral device according to the preceding paragraph(s) may further include an attachment mechanism disposed on at least one of the insert or the activating member, the attachment mechanism being configured to releasably retain the insert and the activating member in operable communication.

In another implementation, in the oral device according to the preceding paragraph(s), the attachment mechanism may include a protrusion extending from the insert or the activating member and a receptacle on the other of the insert or the activating member configured to releasably receive the protrusion.

In other implementations of this disclosure, a kit may include an activating member, a first insert, and a second insert. The activating member may include a housing configured for placement in an oral cavity, and a power source disposed in the housing. The first insert may include a first facial portion comprising a first surface configured for placement proximate a facial surface of the teeth, a first lingual portion comprising a second surface spaced from the first surface and configured for placement proximate a lingual surface of the teeth, a first base connecting the first facial portion and the first lingual portion, the first base, the first surface, and the second surface forming a first channel for receiving the teeth, and a first active agent disposed in the channel for providing a first oral benefit. The second insert may include a second facial portion comprising a third surface configured for placement proximate the facial surface of the teeth, a second lingual portion comprising a fourth surface spaced from the third surface and configured for placement proximate a lingual surface of the teeth, a second base connecting the second facial portion and the second lingual portion, the second base, the third surface, and the fourth surface forming a second channel for receiving the teeth, and a second active agent disposed in the channel for providing a second oral benefit.

In another implementation, in the kit according to the preceding paragraph(s), the first insert may include a first electrode positioned proximate the first surface and a second electrode positioned proximate the first base and the second insert comprising a third electrode positioned proximate the third surface and a fourth electrode positioned proximate the fourth surface, wherein attachment of the first insert to the housing forms an electrical connection to provide power from the power source to the first electrode and the second electrode and wherein attachment of the second insert to the housing forms an electrical connection to provide power from the power source to the third electrode and the fourth electrode.

In another implementation, in the kit according to the preceding paragraph(s), the activating member may include a first connector, the first insert may include a second connector compatible with the first connector, and the second insert may include a third connector compatible with the first connector.

Further areas of applicability of the present disclosure will become apparent from the detailed description provided hereinafter. It should be understood that the detailed description and specific examples, while indicating embodiments of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION

Figure 1:
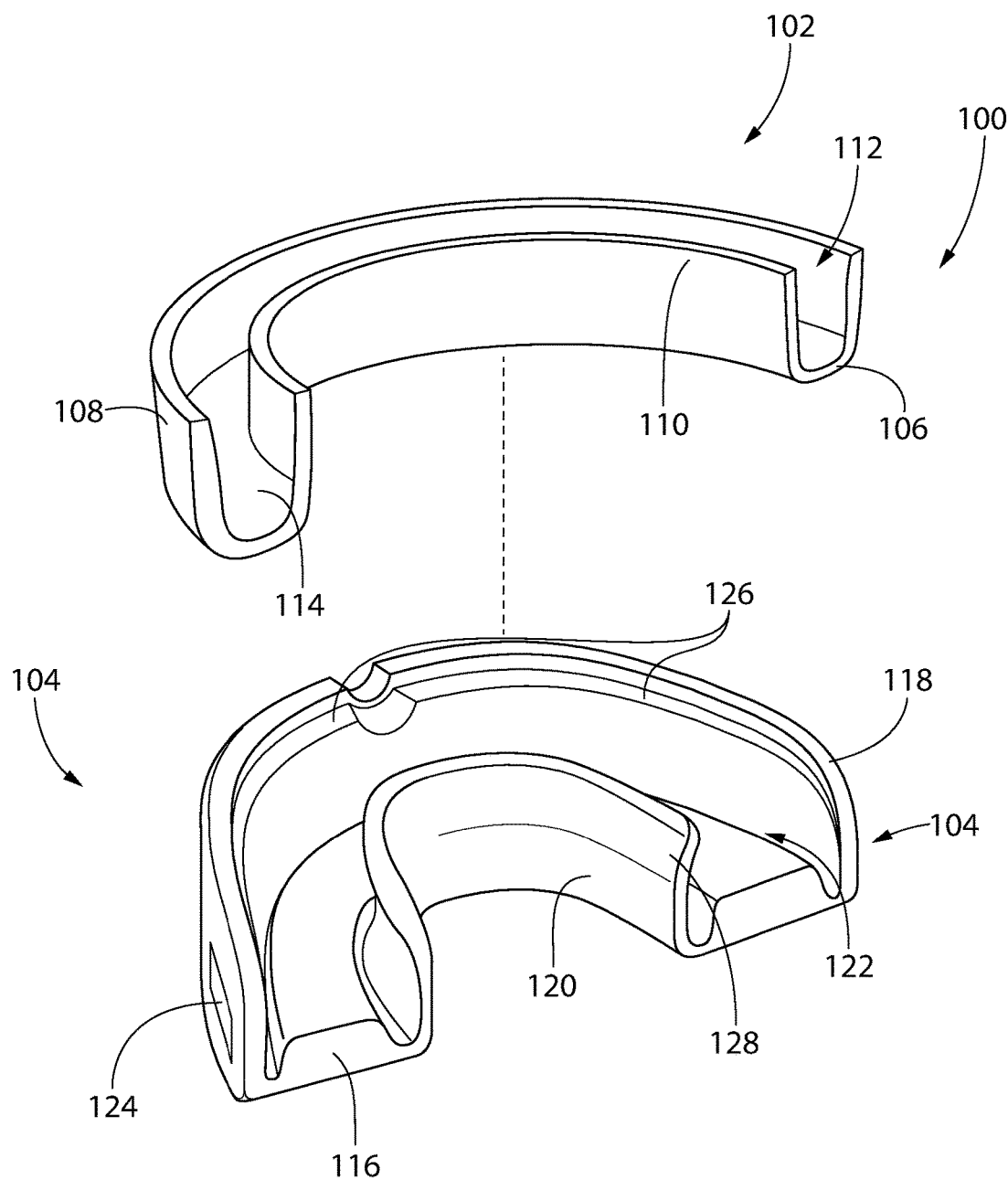
FIG. 1 is an exploded perspective view of an oral care apparatus according to an example implementation of this disclosure.

The following description of the preferred embodiments is merely exemplary in nature and is in no way intended to limit the disclosure, its application, or uses.

As used throughout, ranges are used as shorthand for describing each and every value that is within the range. Any value within the range can be selected as the terminus of the range. In addition, each references cited herein is hereby incorporated by reference in its entirety. In the event of a conflict in a definition in the present disclosure and that of a cited reference, the present disclosure controls.

This disclosure relates generally to oral care implements, and more particularly to multiple-piece devices capable of being placed within the oral cavity to provide a benefit to the oral cavity. In some implementations, the oral device may include an insert carrying an active agent and an activating member that releasably connects to the insert. For example, the insert may be configured for placement on a wearer's teeth, e.g., to place an active agent in contact with the teeth, and the activating member may hold or otherwise retain the insert in position.

In embodiments of this disclosure, the activating member may include a battery or other power source configured to power an activating element that activates or otherwise interacts with the activating agent to provide a benefit to the oral cavity. For instance, the activating element may be a light source disposed on the activating member. Using power from the power source, the light source emits a light that irradiates the teeth, for example. In this example, the activating agent may be hydrogen peroxide and the light is emitted at a wavelength known to increase the tooth whitening capabilities of the hydrogen peroxide. In other embodiments, the activating element may include an electrode pair disposed in proximity of the teeth. The electrode pair may be formed on the activating member, or in other embodiments, the insert includes the electrode pair. In the latter configuration, electrical contacts may be provided on the activating member and the insert to electrically connect the electrodes to the power source disposed on the activating member.

According to embodiments of this disclosure, a compact oral care device may be used to provide a number of oral care benefits. For example, the activating member may be configured for use with a number of different inserts and/or different activating agents. In some embodiments, the insert may be pre-packaged with the activating agent, and disposable after use. As a result of some embodiments of this disclosure, a user may select among different types of inserts to provide different benefits. For instance, a user may use a first insert that includes electrodes and a fluoride solution to direct fluorine ions for strengthening tooth enamel and a second insert that includes hydrogen peroxide and a different electrode configuration or no electrodes for purposes of whitening teeth. Thus, for example, a multi-purpose activating member may be used with different inserts to provide varying benefits.

Although certain embodiments and benefits will be described, other implementations, modifications, and/or benefits will be appreciated by those having ordinary skill in the art, with the benefit of this disclosure. For example, the following detailed description may generally refer to embodiments of the inventive implements in the context of a mouthpiece, but the disclosure is not limited to mouthpieces; other oral care implements may also incorporate features of this disclosure.

FIG. 1 illustrates an oral device 100 according to implementations of this disclosure. The oral device 100 comprises a wearable appliance generally configured as a two-piece mouthpiece. As illustrated, the device 100 includes an insert 102 and an activating member 104. The insert 102 and the activating member 104 preferably are configured for releasable attachment to each other. For example, attachment of the insert 102 to the activating member 104 may provide an appropriate alignment of the insert 102 relative to the activating member 104, and in some embodiments, which will be described in more detail below, the attachment may facilitate powering elements of the insert 102 via a power source on the activating member 104.

As illustrated, the insert 102 may be shaped generally as a bite plate, a mouthguard, an occlusal splint or the like. The shape of the illustrated insert 102 is known in the art, and generally consists of a U-shaped base 106, a facial sidewall or portion 108 extending from the base 106 in a first direction and a lingual sidewall or portion 110 spaced from the facial portion 108 and also extending in the first direction. In this configuration, the base 106, the facial sidewall 108 and the lingual sidewall 110 generally form a tray or channel 112 to receive a wearer's teeth. More specifically, the base 106 is generally configured for positioning to extend along one or more teeth between the maxillary and the mandibular teeth, the facial sidewall 108 is generally configured to extend along a facial surface of the teeth, and the lingual sidewall 110 is generally configured to extend along a lingual surface of the teeth. In some embodiments, the facial sidewall 108 may contact the facial surface of one or more of the teeth and/or the facial sidewall may be arranged near the facial surface of the teeth, but not in direct contact. Similarly, the lingual sidewall 110 may contact the lingual surface of one or more of the teeth and/or the lingual sidewall may be arranged near the lingual surface of the teeth, but not in direct contact. In some implementations, the dimensions of the insert 102 may be customized for a user, or may be provided in one more predetermined or generic sizes. Moreover, although the base is illustrated as being generally perpendicular to the upstanding facial and lingual sidewalls, either or both of the sidewalls and/or the base may be formed at different angles relative to each other. By way of non-liming example, the base may constitute any connection between the lingual and facial sidewalls. For instance, it is contemplated that the lingual and facial sidewalls could terminate at a common point, thereby creating a V-shaped channel, instead of the illustrated U-shaped channel. In this embodiment, the junction between the sidewall constitutes the base.

Insert 102 also includes an active agent 114 disposed in the channel 112. The active agent 114 may be provided to contact one or more surfaces of the teeth when the insert is placed in the oral cavity. For example, the active agent may be a gel, viscous liquid, or the like, that is retained in the channel 112. In other embodiments, the active agent may be retained in a polymer matrix, sponge, or the like that is disposed in the channel 112 and selected to allow for contact of the active agent with the teeth.

The insert 102 is configured for connection to the activating member 104. In the embodiment illustrated in FIG. 1, the activating member 104 is also shaped like a conventional mouthguard. More specifically, the activating member 104 generally includes a U-shaped base 116. A facial wall 118 extends from the base 116 proximate an outer edge of the base 116. A lingual wall 120 also extends from the base 116, generally in the same direction as the facial wall 118, proximate an inner edge of the base 116. The facial wall 118 and the lingual wall 120 extend from the base 116 to form a receptacle 122, which generally includes a U-shaped channel. In embodiments of this disclosure, the spacing between the facial wall 118 in the lingual wall 120 is greater than a distance between exterior surfaces of the facial sidewall 108 and lingual sidewall 110 of the insert 102. In this manner, the insert 102 may be received in the receptacle 122.

As also illustrated in FIG. 1, the activating member also includes a power source, e.g., a battery 124. The battery 124 is illustrated schematically as being disposed on the facial wall 118 of the activating member 104. In some embodiments, the battery 124 may be embedded in the facial wall 118. For instance, the activating member 104 may be overmolded or otherwise formed around the battery 124, such that the battery 124 is located between opposite inner and outer surfaces of the facial wall 118. Similarly, the battery may be disposed on the wall and covered with a protective layer, e.g., to prevent contact of the battery with contaminants in the oral cavity. In other embodiments, the battery 124 may be provided instead on or incorporated into the lingual wall 120 or the base 116. Moreover, multiple batteries 124 may be provided, and such batteries may be disposed on or in any one or more of the base 116, the facial wall 118, and/or the lingual wall 120. The battery 124 may be any power source capable of providing power necessary for operating an activating element (described in detail below). The battery 124 may be a single use battery, which may be replaceable, or in some embodiments, the battery 124 may be rechargeable, e.g., using an external power source (not shown). For example, the battery may be a printed battery, a conventional cell, or the like.

As noted above, the insert 102 is received in the receptacle 122 of the activating member 104. In preferred embodiments of the disclosure, the insert is removably received in the receptacle 122, e.g., for replacement. FIG. 1 illustrates additional features on the activating member 104 that may facilitate retention of the insert 102 relative to the activating member 104. More specifically, a ridge or protrusion 126 may be provided on a surface of the facial wall facing the receptacle 122. In addition, or alternatively, the distal ends 128 of the lingual wall 120 may be in-turned, i.e., toward the receptacle 122. The protrusion 126 and the distal ends 128 operate in a similar manner. Specifically, as the insert 102 is placed into the receptacle 122, i.e., by lowering the insert into the receptacle 122, an outer surface (i.e., opposite the channel 112) of the facial sidewall 108 of the insert 102 passes over the ridges 126 and an outer surface (i.e., opposite the channel 112) of the lingual sidewall 110 of the insert 102 passes over the distal ends 128 of the lingual wall 120. At least one of the facial sidewall 108, the lingual sidewall 110, the facial wall 118, and/or the lingual wall 120 may be deformable 102 to promote pressing of the insert 102 into the receptacle 122. For example, the insert 102 and/or the activating member may be formed of a pliable polymer. Once seated in the receptacle 122, e.g., with the base 106 of the insert 102 contacting the base 116 of the activating member 104, the protrusions 126 are positioned above the top surface of the facial sidewall 108 of the insert 102 and the distal ends 128 of the lingual wall 120 extend above a top surface of the lingual sidewall 110 of the insert 100. More specifically, the insert 102 may be dimensioned such that an outer surface of the facial sidewall 108 and the outer surface of the lingual sidewall 110 form an interference fit with the protrusions 126 and the distal end 128 of the activating member 104, but the ridges 126 and the distal ends 128 are generally positioned above the top of the insert 102 when the insert 102 is properly received in the receptacle 122.

In operation, a user may place the insert in her mouth, positioning her maxillary teeth in the channel 112. With the insert so positioned, the wearer may then place the activating member into the oral cavity below the insert 102 and apply upward pressure, relative to the maxillary teeth, to position the activating member 104 over the insert 102. Alternatively, the wearer may place the insert 102 into the activating member 104 prior to placement in the oral cavity. Once in the oral cavity, an activating element (not shown in FIG. 1), powered by the battery 124, activates the activating agent to treat the teeth or oral cavity. Upon completion of the treatment, the wearer may remove the device 100 from her mouth, lift the insert 102 from the receptacle, e.g., by grasping and pulling the insert 102, and discard the insert 102. In this manner, the activating agent may be contained in the insert, with minimal contact with the activating member. The activating member may be rinsed or otherwise cleaned and placed on a charger, for example, until the next use.

FIG. 1 illustrates a general configuration for an oral device 100 in which a cooperating insert 102 and activating component 104 are provided to render an oral benefit. Many modifications to the illustrated embodiment are contemplated. For example, as illustrated in FIG. 1, the insert 102 is generally configured for placement on the maxillary teeth. In other embodiments, the insert 102 may be configured instead for placement on the mandibular teeth. In still other embodiments, such as described below in connection with FIG. 5, two inserts may be provided, one for placement on the maxillary teeth and another for placement on the mandibular teeth. Moreover, as will be described below in connection with FIGS. 6 and 7, for example, the insert 102 could be configured for placement on both the maxillary and mandibular teeth.

Other modifications may also be made. For example, the protrusions 126 and the in-turned distal ends 128 are only an example arrangement for retaining the insert 102 in the receptacle 122. In some embodiments, only the protrusions 126 or only the in-turned distal ends 128 may be provided. Moreover, distal ends of the facial sidewall 118 may be alternatively or additionally turned inward. Similarly, protrusions like the protrusions 126 may be provided alternatively, or in addition, on the lingual wall 120. Other alignment and/or retention members will be described in more detail below, and still others will be appreciated by those having ordinary skill in the art, with the benefit of this disclosure.

Figure 2A:
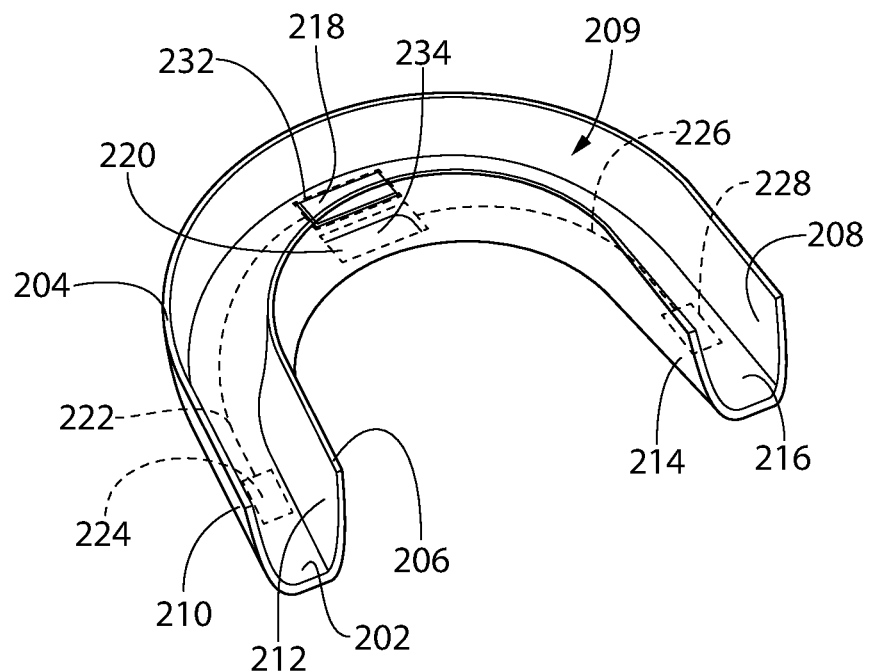
FIGS. 2A and 2B are a top perspective view and a bottom plan view, respectively, of an insert for use in an oral care apparatus according to example embodiments of this disclosure.
Figure 2B:
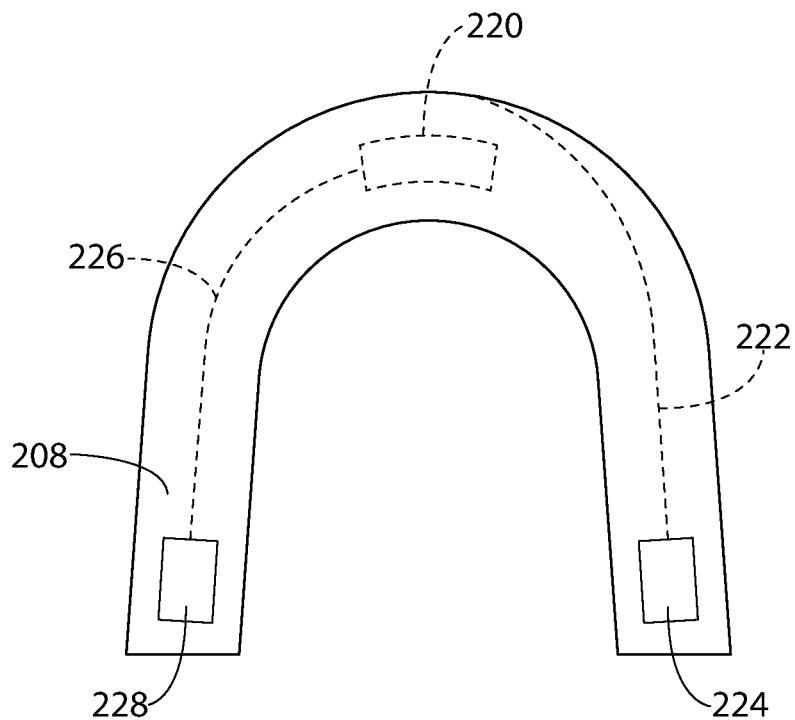
Figure 3A:
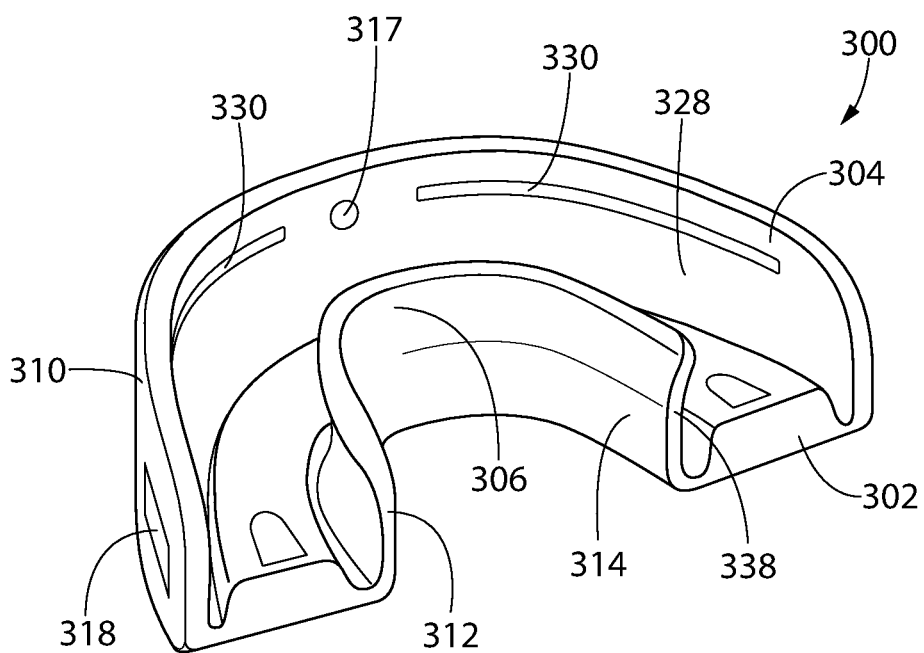
FIGS. 3A and 3B are a top perspective view and a top plan view, respectively, of an activating member for use in an oral care apparatus according to example embodiments of this disclosure.
Figure 3B:
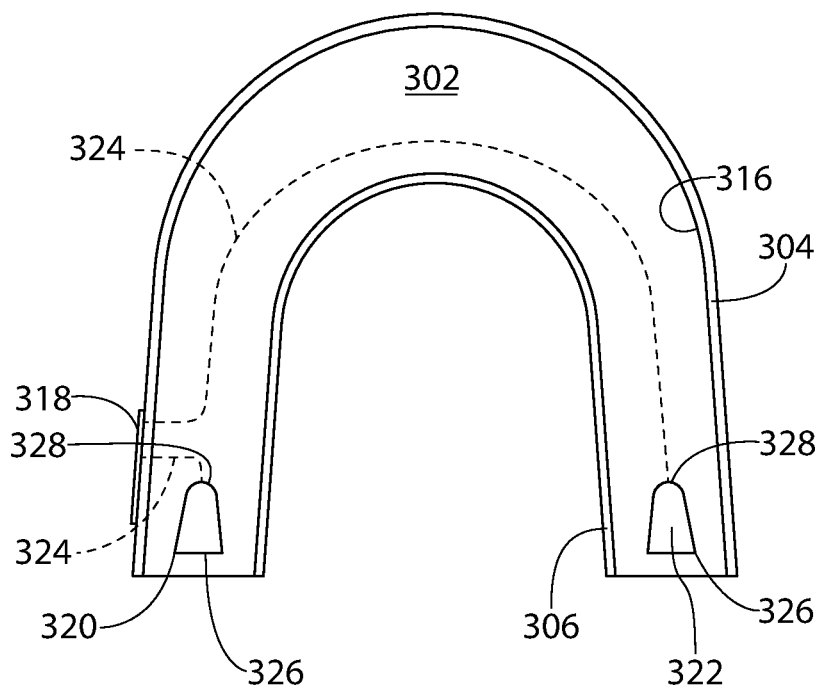

As noted above, the oral device 100 includes an activating element that, in conjunction with an activating agent, delivers one or more oral benefits. FIGS. 2A, 2B, 3A, and 3B illustrate an example of the device 100. Specifically, FIGS. 2A and 2B illustrate an insert 200, which may be the insert 102 described above, that includes electrodes for providing an electrochemical benefit, and FIGS. 3A and 3B illustrate an activating member 300, which may be the activating member 104 described above, attachable to the insert 200 to power the electrodes. The insert 200 and the activating member 300 will now be described in greater detail.

The insert 200 illustrated in FIG. 2 is one, nonlimiting example of the insert 102 illustrated in and described above in connection with FIG. 1. The insert 200 generally includes a base 202, comparable to the base 106 discussed above, a facial sidewall 204, comparable to the facial sidewall 108 discussed above, and a lingual sidewall 206, comparable to the lingual sidewall 110 discussed above. The base 202, the facial sidewall 204, and the lingual sidewall 206 generally define a channel 209, similar to the channel 112. In more detail, the facial sidewall 204 includes an inner surface 208, facing the channel 209, and an opposite, outer surface 210. Similarly, the lingual sidewall 206 includes an inner surface 212 facing the channel 209 and an opposite, outer surface 214. The inner surface 208 of the facial sidewall 204 and the inner surface 212 of the lingual sidewall 206 define the sides of the channel 209 and a top surface 216 of the base 202 defines the bottom of the channel 209. Although not illustrated, as in the embodiment of FIG. 1 an active agent preferably is disposed in the channel 209. For clarity, the activating agent is not included in FIGS. 2A and 2B.

The insert 200 also includes a first electrode 218 and a second electrode 220. The electrodes 218, 220 are spaced from each other. For example, in the illustrated example, the first electrode 218 is disposed generally on the facial sidewall 204, and the second electrode 220 is disposed on the base 202. The electrodes 218, 220 preferably are metallic elements spaced from each other, such that a potential difference between the electrodes causes flow of ions from the first electrode 218 to the second electrode 220, or vice a versa. The electrodes may comprise a thin metallic plate, e.g., having sufficient thinness that the plate can conform to the contours of the sidewall. In other embodiments, the electrodes may be formed from one or more metallic wires and/or a mesh. By way of non-limiting example, the electrodes may include conducting metals such as tin, nickel, gold, platinum, silver, or the like, or mixtures thereof. The electrodes may also include additional conductive or semi-conductive materials, e.g., in film form, including but not limited to, titanium dioxide, zinc oxide, tin oxide, tin(II) dioxide, $Ln_2O_3$ (either n- or p-type), or the like. The first electrode 218 is electrically connected by a lead 222 or other electrical connection to a first electrical contact 224. Similarly, the second electrode 220 is electrically connected by a lead 226 or similar electrical connector to a second electrical contact 228. In the illustrated embodiment, the first electrical contact 224 and the second electrical contact 228 are exposed metallic elements disposed on a bottom surface 230 (i.e., opposite the top surface 216) of the base 202.

The first electrode 218 and the second electrode 220 may be disposed on the inner surface 208 of the facial sidewall 204 and the top surface 216 of the base 202, respectively. In other embodiments, including the illustrated embodiment, the first electrode 218 may be spaced behind the inner surface 208 of the facial sidewall 204, and/or the second electrode 220 may be disposed below the top surface 216 of the base 202. In this embodiment, the electrodes 218, 220 are exposed to the channel 209 via cutouts 232, 234, which may be voids formed in the inner surface 208 and the top surface 216, respectively. The cutouts 232, 234 serve as windows or openings to expose the electrodes 218, 220, but may prevent direct contact of a wearer's teeth with the electrode, e.g., because the wearer's tooth will contact the relative surface, instead of the electrode, which is offset, behind the surface. In the illustrated embodiment, the electrodes 218, 220 are disposed in the facial sidewall 204 and the base 202, respectively. More specifically, the electrodes 218, 220 are substantially planar metallic plates, and the first electrode 218 is disposed between the inner surface 208 on the outer surface 210 of the facial sidewall 204, and the second electrode 220 is disposed between the top surface 216 and the bottom surface 230 of the base 202. In other embodiments, the first electrode 218 may be disposed or otherwise attached to the outer surface 210 of the facial sidewall 204, with the cutout 232 providing exposure of the electrode 218 to the channel 209. Similarly, the second electrode 220 may be disposed on the bottom surface 230 of the base 202, with the cutout 234 providing exposure of the electrode 220 to the channel 209.

Although the leads 222, 226 are illustrated as being embedded within the base and/or the facial sidewall 204, such is not required. In other embodiments, the leads 222, 226 may be electrically conductive traces formed on one of the surfaces of the insert 200 or embedded in one or more other surfaces. Moreover, although the electrodes 218, 220 are illustrated in one position, modifications are contemplated. For example, the second electrode 220 may be disposed on the inner surface 212 of the lingual sidewall 206. In still other embodiments, the electrodes may be disposed at least partially on the base 202 and at least partially on the lingual sidewall 206. Both electrodes may also be provided on the same surface, e.g., both on the facial sidewall, spaced from each other. In still other embodiments, additional electrodes may be provided. For example, multiple first electrodes 218 may be provided on the facial sidewall, with corresponding second electrodes 220 being provided on the base 202 and/or lingual sidewall 206. Moreover, the electrodes may take shapes and forms other than those illustrated.

FIGS. 3A and 3B illustrate an activating member 300 that can be used with the insert 200 just described. The activating member 300 is similar to the activating member 104 illustrated in FIG. 1, in that it is intended to releasably receive the insert 200. The activating member 300 generally includes a base 302, similar to the base 116 illustrated in FIG. 1, a facial wall 304, similar to the facial wall 118 illustrated in FIG. 1, and a lingual wall 306 similar to the lingual wall 120 illustrated in FIG. 1. The facial wall 304 generally includes an inner surface 308 and an outer surface 310. Similarly, the lingual wall 306 includes an inner surface 312 and an outer surface 314. The inner surface 308 of the facial wall 304, the inner surface 312 of the lingual wall 320, and a top surface 316 of the base 302 generally define a receptacle 317, similar to the receptacle 122 of the activating member 104.

The activating member 300 also includes a power source, such as a battery 318, which may be similar to the battery 124 discussed above. The battery 318 is illustrated as being disposed of the outer surface 310 of the facial wall 304. However, the battery 124 may be located in a different location on the activating member 300. Moreover, additional batteries may be provided in other or additional locations. The battery 318 is electrically coupled to a first electrical contact 320 and a second electrical contact 322, e.g. via leads 324. The first electrical contact 320 and the second electrical contact 322 may comprise an exposed conductive material, located proximate the top surface 316 of the base 302. In some embodiments, the electrical contacts 320, 322 may protrude above the top surface 316 of the base 302. For example, each of the electrical contacts 320, 322 may have a first end 326 fixed relative to the base 302 and an opposite, free end 328. The free ends 328 of the contacts 320, 322 may move relative to the base 302, i.e., by pivoting about the first ends 326. In other embodiments, the contacts 320, 322 may be formed of a domed or convex structure that protrudes above the top surface 316 of the base 302.

In operation, when the insert 200 is placed in the receptacle 317 of the activating member 300, the first electrical contact 224 of the insert 200 contacts the first electrical contact 320 of the activating member 300. Similarly, the second electrical contact 228 of the insert 200 contacts the second electrical contact 322 of the activating member 300. By this electrical contact, power from the battery 318 is provided to the electrodes 218, 220 of the insert 200.

The arrangement and position of the first and second electrical contacts 320, 322 of the activating member 300 and the first and second electrical contacts 224, 228 of the insert 200 may be altered without departing from the scope of this disclosure. For instance, in some embodiments, it may be possible to provide only a single electrical contact on each of the insert 200 and the activating member 300. More than two electrical contacts may also be provided. In other embodiments, the electrical contacts may be positioned on the facial and/or lingual sidewalls and walls of the insert and activating member. Furthermore, although the first electrical contact 224 and the second electrical contact 228 are illustrated as generally planar while the first and second electrical contacts 320, 322 of the activating member 300 are shown as being offset from the top surface 316, such is not required. In some examples, the electrodes on the insert and the electrodes on the activating member may be planar, while in other embodiments, electrodes on the insert may be offset, e.g., relative to the bottom surface 230 of the base 202. In still other embodiments both the electrodes on the insert 200 and electrodes on the activating member 300 may be offset. Moreover, the electrical contacts on the insert may include at least one planar contact and at least one offset contact and/or electrical contacts on the activating member 300 may include at least one planar contact and at least one offset contact. As will be appreciated, many combinations and structures may be used that allow for power from the battery 318 to be communicated to the electrodes 218, 220 on the insert 200 when the insert 200 and the receptacle are operatively connected.

As also illustrated in FIGS. 3A and 3B, the activating member 300 may include features for retaining the insert 200 in the receptacle 317. For example, the activating member 300 includes ridges 330 similar to the protrusions 126 discussed above. As with the protrusions 126, the ridges 330 may be configured to provide an interference fit with the outer surface 210 of the facial sidewall 204 as the insert is placed into the receptacle 317, and is arranged to be above a top surface of the facial sidewall 204 when the insert 200 is completely seated in the receptacle 317. Distal ends 332 of the facial wall 304 may also be in-turned, as with the embodiment described above in connection with FIG. 1. Other retaining features, including those discussed above or below, may also or alternatively be used in the foregoing embodiment.

FIGS. 2A, 2B, 3A, and 3B illustrate an example device according to this disclosure, in which the insert and an activating member are securable to each other to provide an oral benefit. For instance, by providing a potential difference across the electrodes 218, 220, an oral benefit may be provided to the teeth by transferring ions from the activating agent between the electrodes, and into the teeth. For example, the activating agent may include zinc and the electrodes may be operable to cause transport of zinc ions between the electrodes. More specifically, because the insert 200 places the wearer's teeth between the electrodes, zinc ions may be delivered to the tooth.

Figure 4:
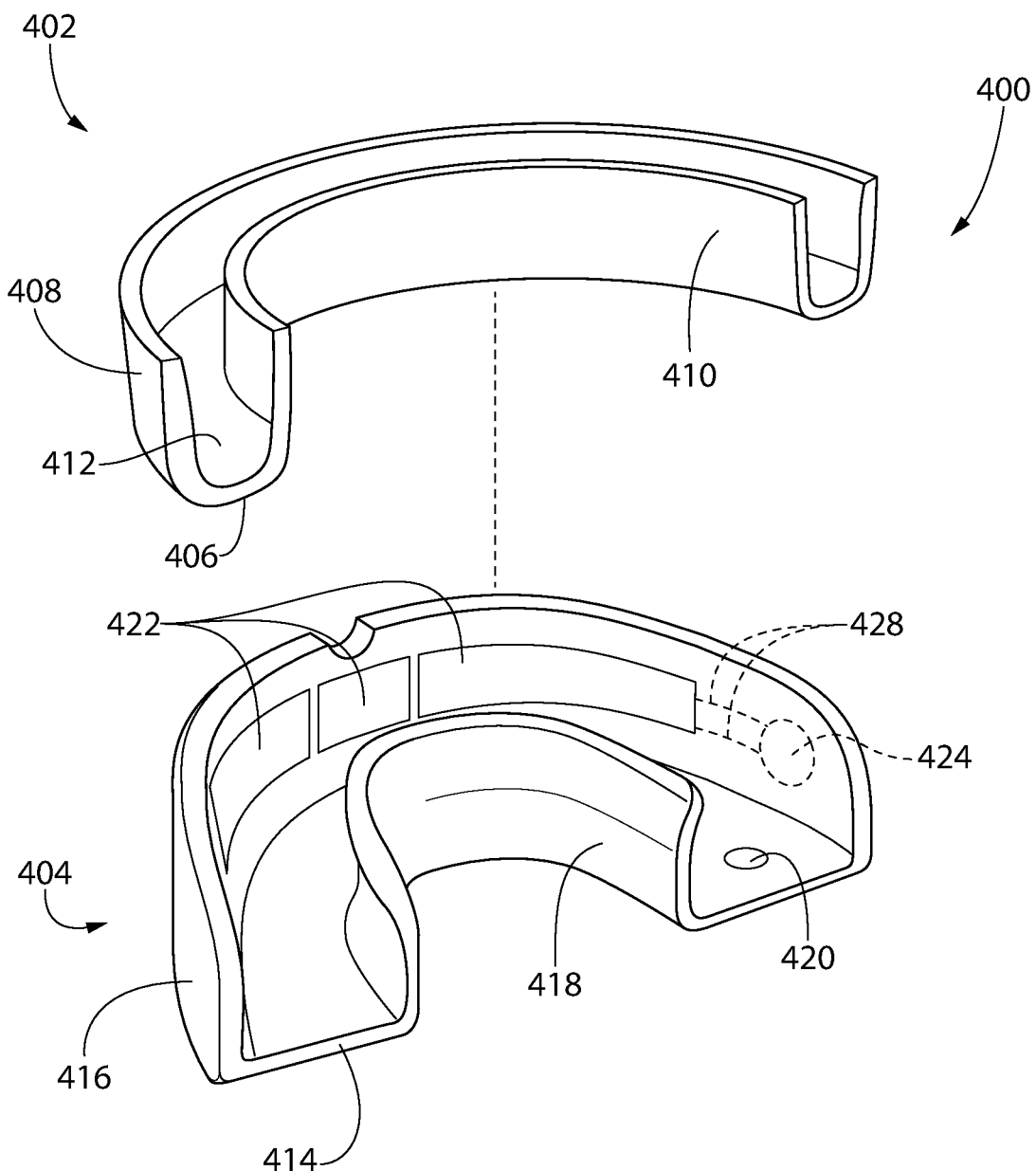
FIG. 4 is an exploded perspective view of another oral care apparatus according to example implementations of this disclosure.

FIG. 4 is an example embodiment of another device 400 according to another embodiment of this disclosure. In the device 400, a light source is provided as the activating element, instead of electrodes as in the previously described embodiment. As with previous embodiments, the oral device 400 generally includes an insert 402 selectively receivable by an activating member 404. The insert 400 to a similar to those discussed above, and generally includes a base 406, a facial sidewall 408, and a lingual sidewall 410. Facial sidewall 408, the base 406, and the lingual sidewall 410 generally form a U-shaped channel 412. Although not illustrated, an activating agent is provided in the channel 412. The form and function of the insert 402 are generally identical to those of the insert 102 discussed above, and thus the details will not be restated herein.

The activating member 404 is also generally similar to the activating member 104 and the activating member 300 discussed above. For example, the activating member 404 generally includes a base 414, a facial wall 416, and a lingual wall 418 spaced from and generally parallel to the facial wall 416. The base 414, the facial wall 416, and the lingual wall 418 generally form a receptacle 420 sized to receive the insert 402.

Unlike in previous embodiments, however, the activating member 404 includes one or more light sources 422 (three are shown, but more or fewer may be provided). The light sources may be, for example, light emitting diodes (LEDs), although other light sources, including but not limited to lasers, may be used. As illustrated, the light sources 422 are disposed on the facial wall 416 of the activating member 404 and are configured to emit light into the channel 420. The light sources 422 may be controllable to emit light at different wavelengths, for example. As also illustrated in FIG. 4, the light sources 422 are powered by a battery 424 (although a power source other than the battery 424 may be used) via one or more leads 426. As with previous embodiments, the position of the battery 424 and the leads 426 may be varied without departing from the spirit and scope of this disclosure. In operation, the insert 402 is placed in the receptacle 420 of the activating number 404 and the light sources 422 are activated. An activating agent (not shown) contained in the channel 412 of the insert is in intimate contact with the teeth, and the light sources 422 illuminate the activating agent and teeth to provide an oral benefit. By way of non-limiting example, the activating agent may include hydrogen peroxide and the light source may be at a predetermined wavelength to excite the hydrogen peroxide to provide an enhanced whitening benefit to the teeth contained in the channel 412 of the insert 402.

As will be appreciated from FIG. 4, light emitted from the light source 422 must pass through the facial sidewall 408 of the insert 402 before contacting the wearer's teeth. Moreover, although the light sources 422 is generally illustrated as being exposed to the channel 420, the light source 422 may be embedded in the facial wall 416 of the activating member 404. In this manner, material comprising the facial wall 416 or some other material, e.g., a covering or the like, may be formed over the front of the light sources 422, such that light emitted from the light sources will pass through some material prior to entering the channel 420. Because of the possibility of light diffraction/refraction caused by the insert 402 and any other material, including a portion of the facial wall 416 through which the light may pass, the composition of the facial sidewall 408 of the insert 402 the composition of the facial wall 416 of the activating member 414, and/or the composition of any covering may be chosen according to the application. For instance, when indigo wavelengths on the order of about 400 to 410 nm are used, it may be desirable that light emitted is not excessively absorbed by the insert 402, the facial wall 416, or other material. Accordingly, the refractive index of the activating member 404 and any material of the facial wall 416 of the activating member 404 may be matched with the materials comprising the facial sidewall 408 of the insert 402 to achieve a minimum level of light loss. This may be particularly important if the light sources are not laser-based, and instead follow the Lambert cosine law in light distribution. More specifically, it may be desirable that the light emitted by the light sources travel through only a single type of material, and that that material is particularly chosen for the application.

A number of materials have been found to have favorable transmission profiles and can be used in applications according to this disclosure. ECTFE Halar 500 LC, PCDF Solef 9009, Solvay Radel R-5000 NT, PPSU Radel R-5000 CL301, and SKC Skyrol Polyester Film AH82L are non-limiting examples of commercially available polymers that have been tested and may be used in embodiments of the present disclosure. For example, these materials have desirable light transmissivities, and are approved for use in the oral cavity. In some embodiments, the material used for the facial sidewall 408 (and in some instances, the facial wall 416) may allow for 80-100% transmission of light at the predetermined wavelength. In some instances, an ideal refractive matching may result in no more than 20% irradiance loss.

In the example of FIG. 4, the light source provides an active benefit instead of the electrode(s) described in other embodiments of this disclosure. However, the insert and/or the activating member may also include one or more electrodes, for example, to provide an electro-chemical benefit in addition to the light-based benefit. For example, the electrodes may be sufficiently thin and/or formed of transparent or translucent conductive materials that irradiating light can pass through the electrodes.

Figure 5:
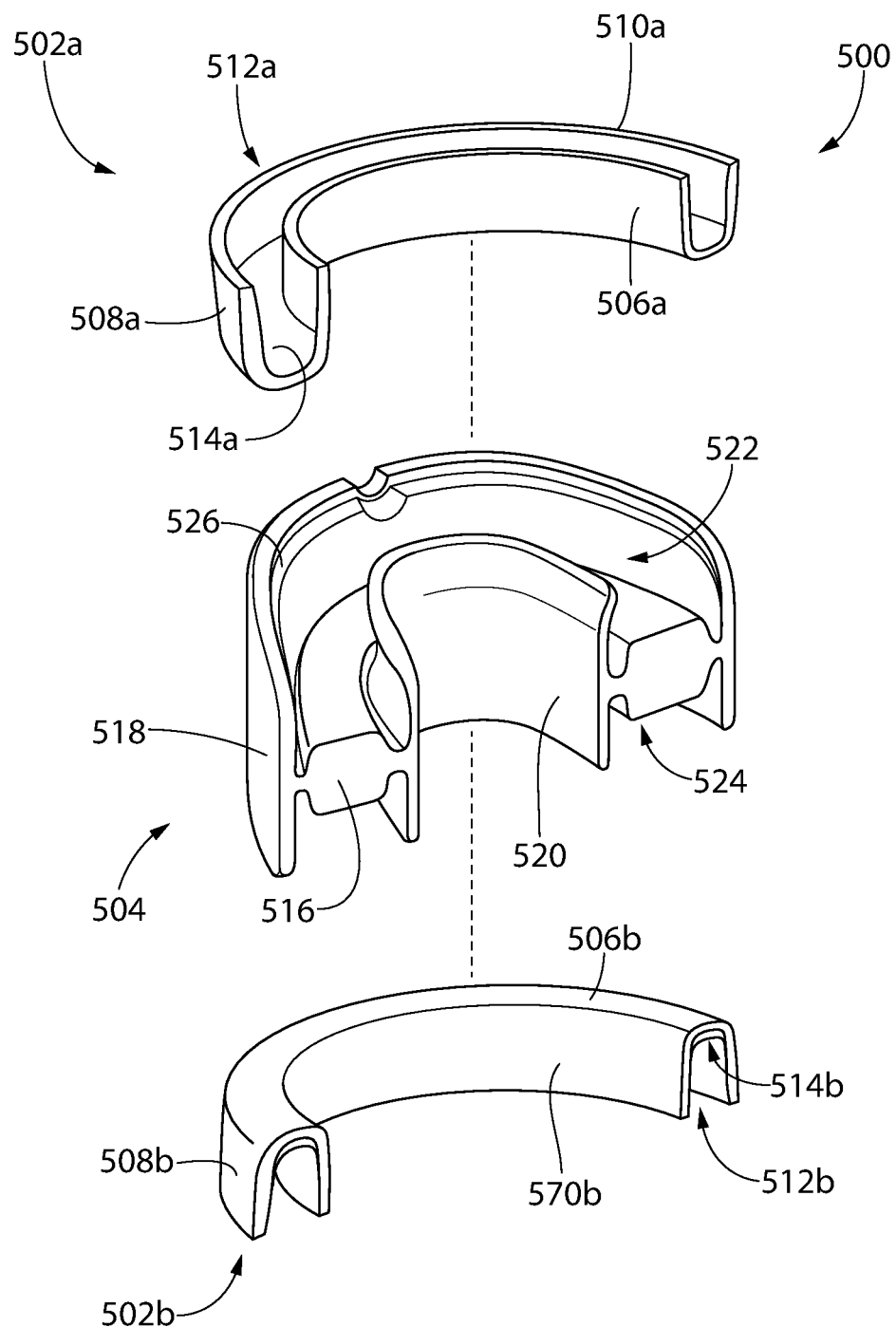
FIG. 5 is an exploded perspective view of yet another oral care apparatus according to an example implementation of this disclosure.

FIG. 5 illustrates yet another example of an oral device 500 according to embodiments of this disclosure. The oral device 500 is similar to the device 100 described above in connection with FIG. 1, but differs in that it provides an oral benefit to both the maxillary teeth and the mandibular teeth.

More specifically, as illustrated in FIG. 5, the oral device 500 includes a first insert 502a and a second insert 502b. The first insert 502a is generally configured for placement over the maxillary teeth of a wearer, and the second insert 502b is generally configured for placement over the mandibular teeth of the wearer. Both the first and second inserts 502a, 502b are configured for connection with an activating member 504. In more detail, each of the inserts 502a, 502b generally includes a base 506a, 506b, a facial sidewall 508a, 508b, and a lingual sidewall 510a, 510b. The respective bases, facial sidewalls, and lingual sidewalls of the inserts 502a, 502b form channels 512a, 512b, and activating agents 514a, 514b are disposed in the respective channels 512a, 512b. Thus, each of the insert 502a, 502b is substantially identical to the insert 102 discussed above.

The activating member 504 generally includes a base 516, a facial wall 518 and a lingual wall 520. The facial wall 518 and the lingual wall 520 extend both above and below the base 516, to form an upper receptacle 522 above the base 516, and a lower receptacle 524 below the base 516. In addition, the activating member 504 may also include one or more ridges 526, which may function like the ridges and protrusions discussed above, to help retain the inserts 502a, 502b in the respective receptacles 522, 524. As will be appreciated, and although not illustrated, the activating member 504 also includes a power source, such as a battery, for powering an activating element (not shown). For instance, the activating element may include electrodes disposed on the insert, as in the embodiment illustrated in FIGS. 2A, 2B, 3A, and 3B, or a light source disposed on the activating member 504 in the embodiment of FIG. 4. In other embodiments, the activating member 504 may include both the light source and contacts via which electrodes on an insert may be electrically connected to a power source on the activating member 504. In this manner, the activating member 504 may be useful to provide a light-based benefit, as well as to provide for electrical connection to some other benefit, such as an electrochemical benefit, provided by the insert.

Figure 6A:
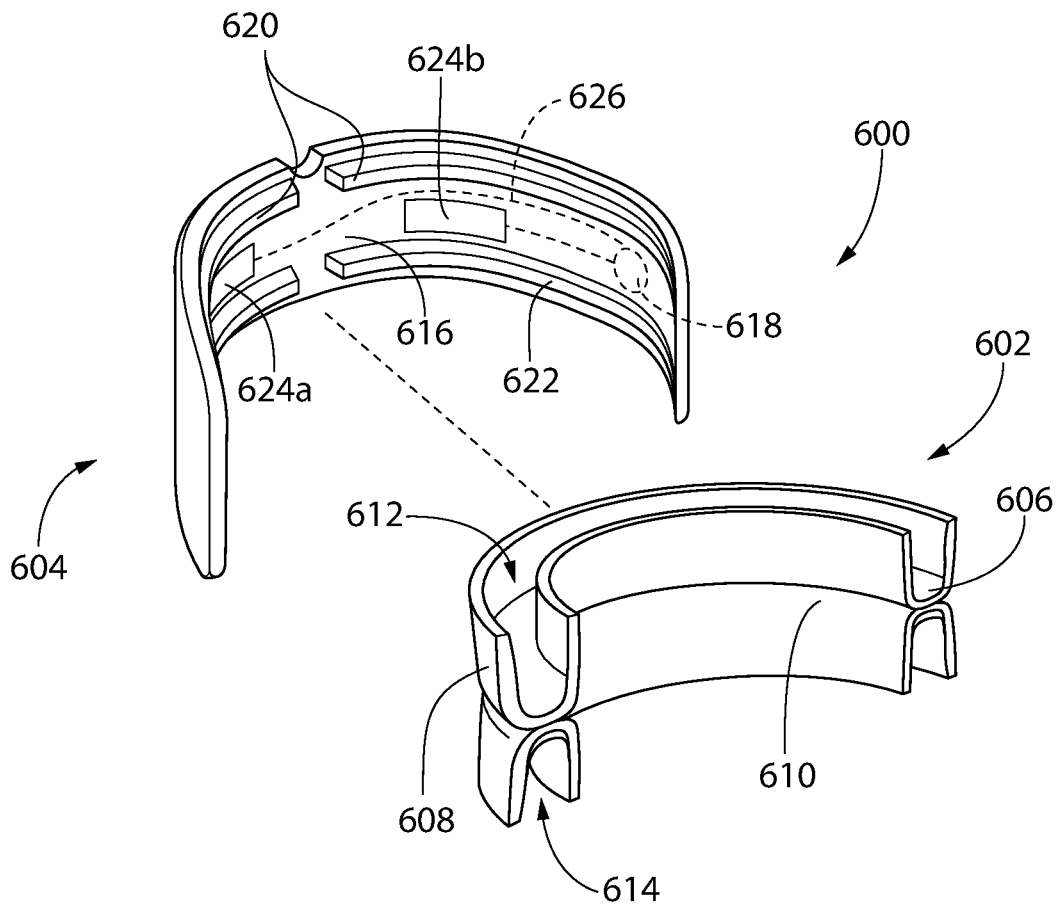
FIG. 6A is an exploded perspective view of still another oral care apparatus including an insert and an activating member, according to an example implementation of this disclosure.
Figure 6B:
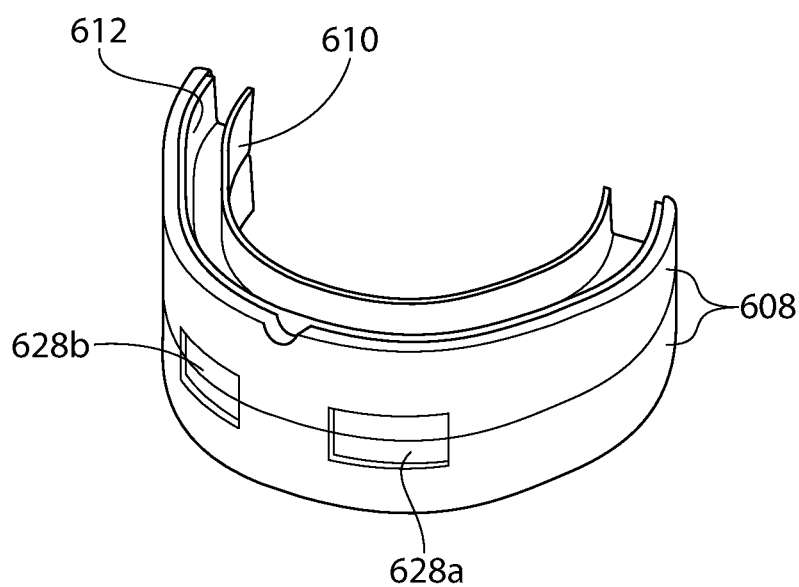
FIG. 6B is another perspective view of the insert illustrated in FIG. 6A.

FIG. 6 illustrates yet another example device 600 according to embodiments of this disclosure. The oral device 600 includes an insert 602 configured for placement on both the maxillary teeth and the mandibular teeth of a wearer and an activating member 604 operably connectable to the insert 602.

As illustrated, the insert 602 generally includes a base 606, a facial sidewall 608, and a lingual sidewall 610, as in previous embodiments. Unlike previous embodiments, however, the facial sidewall 608 and the lingual sidewall 610 depend both above and below the base 606, thereby forming a top channel 612 and a bottom channel 614. The top channel 612 is generally configured to receive the maxillary teeth of the wearer and the bottom channel 614 is generally configured to receive the mandibular teeth of the wearer.

Also unlike previous embodiments, the activating member 604 does not include a U-shaped receptacle for receiving the insert. Instead, the activating member 604 generally includes a facial surface 616 configured to extend along a portion of the facial sidewall 608 of the insert 602. As illustrated, a battery 618 or other power source is embedded in the facial surface 616. Also, a top protrusion 620 and a bottom protrusion 622 extend outwardly from the facial surface 616. In this embodiment, when the facial surface 616 of the activating member 604 is placed in contact with the facial portion 608 of the insert 602, the top protrusion 620 extends generally along a top surface, or just above the top surface, of the facial sidewall 608. Similarly, the bottom protrusion 622 extends generally along a bottom surface, or just below the bottom surface, of the facial sidewall 608. The facial surface 616 may be a relatively thin surface that may be retained in contact with the insert 602 by the wearer's lips, with the protrusions 620, 622 limiting sliding of the activating member 604 relative to the insert 602.

As also illustrated in FIG. 6, first and second electrical contacts 624a, 624b also are provided on the facial surface 616. The contacts 624a, 624b are electrically connected to the battery 618 via leads 626. Cooperating electrical contacts 626a, 626b are provided on the outer surface of the facial sidewall 608 of the insert 602. Although not illustrated, the contacts 626a, 626b may be electrically connected to electrodes disposed in one or both of the channels 612, 614, for example, in a manner similar to that described above with reference to FIGS. 2A and 2B. In another embodiment, the electrical contacts 626a, 626b may not be provided, and the electrical contacts 624a, 624b may be replaced with one or more light sources, such as the light source(s) described above with reference to FIG. 4.

In operation, the user may place the insert 602 in her mouth, and clench her teeth to place maxillary teeth in the top channel 612 and mandibular teeth in the bottom channel 614. Once in place, the user may then insert the activating member 604 behind her lips such that the facial surface 616 contacts the facial sidewall 608 of the insert 602. As noted above, the protrusions 620, 622 may prevent relative sliding of activating member 604 relative to the insert 602, and the wearer's lips will provide sufficient force to maintain contact between the facial surface 616 of the facial sidewall 608. Other embodiments may include a coupling member for creating a positive coupling between the activating member 604 and the insert 602. For example, a first magnet may be provided proximate the facial surface 616 and a second magnet or metallic surface that is attracted to the first magnet may be provided on the outer surface of the facial sidewall 608 of the insert 602.

Figure 7:
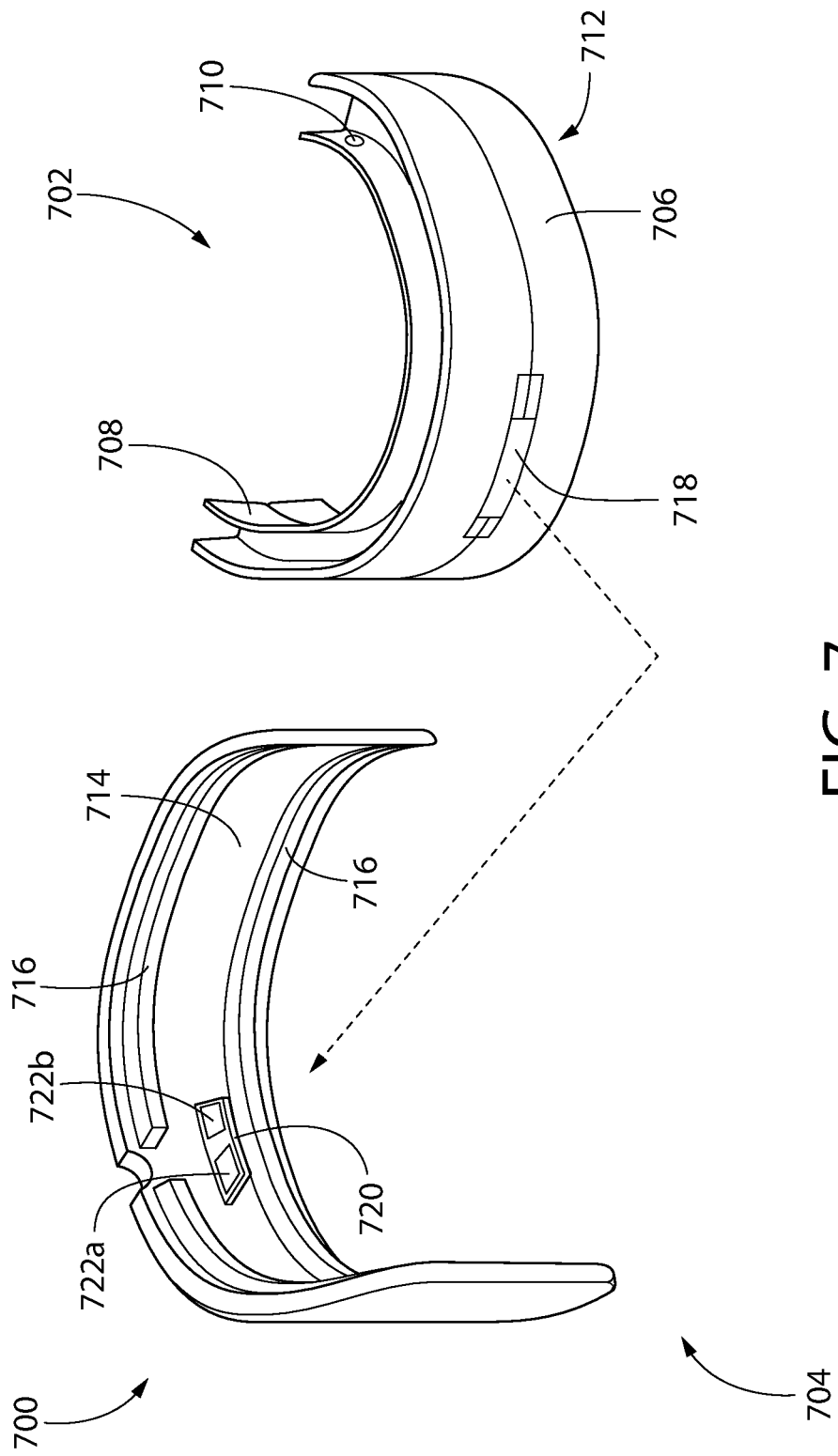
FIG. 7 is an exploded perspective view of still another oral care apparatus according to an example implementation of this disclosure.

Other modifications also are contemplated. For example, FIG. 7 illustrates an oral device 700 comprising an insert 702 similar to the insert 602, and an activating member 704 similar to the activating member 604. The insert 702 includes a facial sidewall 706 and a lingual sidewall 708 defining opposing sides of a top channel 710 and a bottom channel 712, as described above. The top channel 710 is generally configured to receive the maxillary teeth and the bottom channel 712 is generally configured to receive the mandibular teeth. The activating member 704 comprises a facial surface 714 and protrusions 716 similar to the top and bottom protrusion 620, 622.

Unlike the embodiment just described, however, a receptacle 718 is formed as an opening in the facial sidewall 706 of the insert 702 and a mating projection 720 depends from the facial surface 714 of the activating member 704. In this embodiment, the projection 720 is inserted into the receptacle 718 to maintain a desired attachment and/or alignment of the activating member 704 relative to the insert 702. In some embodiments, the projection 720 may form an interference fit with the receptacle 718. In other embodiments, the projection 720 may include a detent or other mechanism that helps to retain the projection 720 in the receptacle 718. The receptacle 718 and the projection 720 may also obviate the need for the protrusions 716.

Moreover, although the projection 720 and the receptacle 718 may provide for a positive attachment of the activating member 704 to the insert 702, these features may provide additional benefits. For example, as also illustrated in FIG. 7, electrical contacts 722a, 722b may be disposed on the attachment projection 720 such that when the projection 720 is placed in the receptacle 718, the electrical contacts 722a, 722b come into contact with cooperating contacts disposed in the receptacle 718. For instance, the electrical contacts 722a, 722b may be electrically connected to a battery (not shown) disposed on the activating number 704 and thereby provide power to the insert 702. Although the electoral context contacts 722a, 722b are illustrated as being disposed on the top surface of the projection 720, such is not required. For instance, one or more of the contacts may be exposed on an opposite, bottom surface of the projection 720.

As detailed above, the various inserts are designed to retain an activating agent. The activating agent may provide a direct benefit to the oral cavity, or may provide a benefit to the oral cavity in connection with an activating element, such as the light sources and/or electrodes discussed in detail above. In some implementations, a user may purchase or otherwise obtain the insert without an activating agent. Thus, it may be up to the user to place the activating agent into the insert. For instance, the user may separately obtain the activating agent (e.g., in a bulk container) and using conventional means and mechanisms, place the activating agent into the insert before placing the insert in the user's mouth. As noted above, the activating agent may be provided as a gel, a liquid, or in any other form. Moreover, the insert may be provided with a sponge or other absorptive material to aid in retaining the activating agent in the insert, e.g., when the activating agent is a liquid.

In other embodiments, the activating agent may be pre-placed in the insert, e.g., at the time of manufacture. For instance, a gel can be applied in the insert prior to packaging and commercial use. In other embodiments, the activating agent may be retained in a polymer matrix that is used to form a portion of the channel or other segment of the insert. When the activating agent is placed in the insert and the insert is subsequently packaged, packaging may be selected to retain an efficacy of the activating agent, for example, by inhibiting contaminants from contacting the activating agent. The activating agent may include a soluble material that becomes fluid in the presence of the user saliva. Thus, the activating agent would not spill from the insert, but would become liquid or more flowable once exposed to conditions in the oral cavity.

Figure 8:
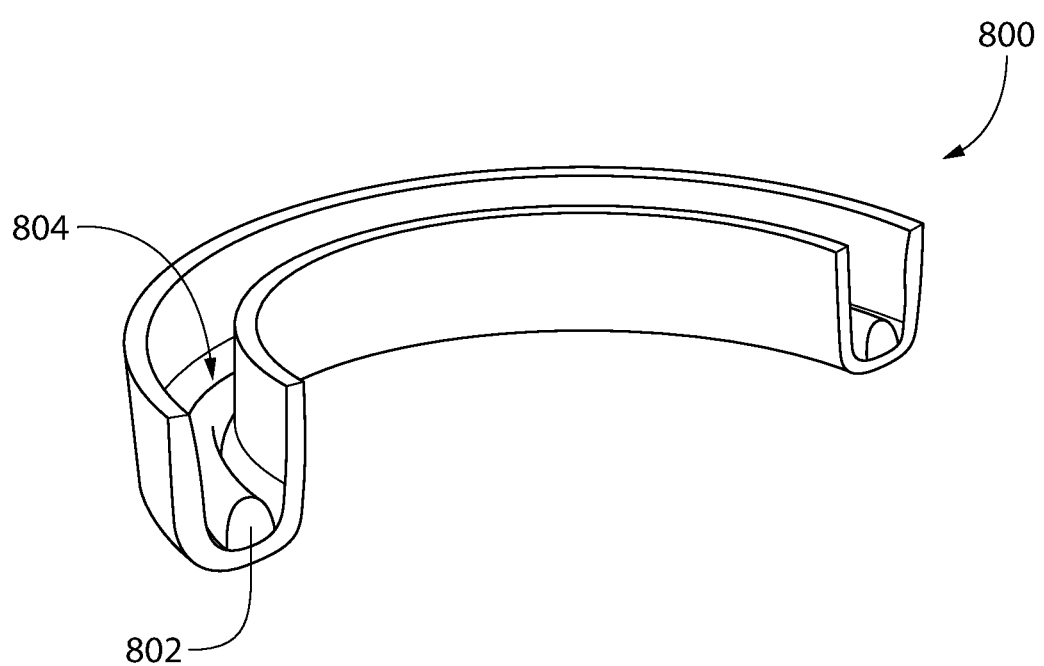
FIG. 8 is perspective view of an alternative oral care apparatus according to an additional example implementation of this disclosure.

FIG. 8 illustrates yet another embodiment of an insert 800 with an activating agent. More specifically, the insert 800 includes a reservoir 802 disposed in a channel 804. The reservoir 802 may comprise a thin polymer barrier or membrane that acts as a container for an activating agent. The activating agent may be liquid, gel, or solid. The reservoir 802 may be formed from sufficiently thin material, or may include weakened areas, such that when the user bites down with the insert properly positioned, the user's teeth will puncture or rupture the reservoir, thereby releasing the activating agent contained therein. In other embodiments, a needle or other piercing element may be disposed on the activating member such that proper connection of the insert 800 to an activating member, e.g., the activating member 104, 300, or 404, will cause the reservoir 802 to rupture.

The present disclosure describes oral care devices that are effective and relatively simple to use. The devices described herein may provide a therapeutic effect within the oral cavity with minimal user interaction. Moreover, devices described herein may allow a user to administer therapeutic agents to obtain different benefits using a single activating member.

Although example embodiments have been described in language specific to the structural features and/or methodological acts, the claims are not necessarily limited to the specific features or acts described. Rather, the specific features and acts are disclosed as illustrative forms of implementing the example embodiments.

What is claimed is:

1. An oral device comprising:
    an insert configured for placement in an oral cavity in contact with teeth in the oral cavity, the insert comprising:
        a facial portion comprising a first surface configured for placement proximate a facial surface of the teeth;
        a lingual portion comprising a second surface spaced from the first surface and configured for placement proximate a lingual surface of the teeth;
        a base connecting the facial portion and the lingual portion, the base, the first surface, and the second surface forming a channel for receiving the teeth;
        a first electrode arranged proximate the first surface;
        a second electrode spaced from the first electrode; and
        at least one first electrical connector electrically connected to at least one of the first electrode or the second electrode; and
    an activating member configured for placement in the oral cavity, the activating member comprising:
        a housing configured to be completely received in the oral cavity;
        a power source disposed in the housing; and
        at least one second electrical connector electrically connected to the power source, the at least one second electrical connector being connectible to the at least one first electrical connector to supply power from the power source in the activating member to the first electrode and the second electrode in the insert.

2. The oral device of claim 1, wherein the housing comprises a housing base, an arcuate housing facial wall extending from a top surface of the housing base, and an arcuate housing lingual wall extending from the top surface and spaced from the lingual wall.

3. The oral device of claim 2, wherein a third surface of the facial wall, a fourth surface of the lingual wall facing the third surface, and the top surface of the base form at least part of a receptacle configured to receive the insert.

4. The oral device of claim 2, wherein a spacing between the third surface and the fourth surface provides an interference fit between the activating member and an outer surface of the insert.

5. The oral device of claim 2, wherein a spacing distance between the third surface and the fourth surface varies at discrete distances from the top surface of the housing base.

6. The oral device of claim 2, wherein the spacing is smaller at a first location farther from the top surface than at a second location closer to the top surface.

7. The oral device of claim 6, wherein the facial portion comprises a first facial portion and the lingual portion comprises a first lingual portion, and the channel is configured for receiving maximal teeth of the teeth, insert further comprising:
a second facial portion extending, relative to the base, in a substantially opposite direction as the first facial portion, the second facial portion comprising a third surface configured for placement proximate a facial surface of mandibular teeth in the oral cavity; and
a second lingual portion extending, relative to the base, in a substantially opposite direction as the first lingual portion, the second lingual portion comprising a fourth surface configured for placement proximate a lingual surface of the mandibular teeth, the third surface, the fourth surface, and the base forming at least a portion of a second channel for receiving the mandibular teeth.

8. The oral device of claim 7, wherein the housing comprises an arcuate housing facial wall configured to contact at least one of an outer surface of the first facial portion or an outer surface of the second facial portion.

9. The oral device of claim 7, wherein one of the activating member or the insert comprises a protrusion and the other of the activating member or the insert comprises a receptacle for releasably receiving the protrusion.

10. The oral device of claim 9, wherein the first electrical connector is disposed on the protrusion or in the receptacle and the second electrical connector is the other of disposed on the protrusion or in the receptacle.

11. An oral device comprising:
an insert configured for placement in an oral cavity, the insert comprising:
a facial portion comprising a first surface configured for placement proximate a facial surface of teeth within the oral cavity,
a lingual portion comprising a second surface spaced from the first surface and configured for placement proximate a lingual surface of the teeth,
a base connecting the facial portion and the lingual portion, the base, the first surface, and the second surface forming a channel for receiving the teeth, and
an active agent disposed in the channel; and
an activating member configured for placement in the oral cavity and releasably retained in operable communication with the insert, the activating member comprising a power source for powering an electronic element that cooperates with the active agent to apply a benefit to the teeth and a receptacle to receive the insert;
wherein the insert comprises a first electrical contact disposed on an external surface of the insert, opposite the channel;
wherein the activating member comprises a second electrical contact on an interior surface of the receptacle; and
wherein positioning of the insert in the receptacle places the first electrical contact in contact with the second electrical contact.

12. The oral device of claim 11, wherein the insert further comprises a first electrode disposed proximate the first surface and a second electrode disposed proximate at least one of the second surface or the base.

13. The oral device of claim 11, further comprising a first electrical contact on the insert and a second electrical contact on the activating member in electrical communication with the power source, wherein the first electrical contact and the second electrical contact are electrically connected when the activating member is placed in operable communication with the insert.

14. The oral device of claim 11, wherein the receptacle of the activating member is U-shaped.

15. The oral device of claim 11, further comprising an attachment mechanism disposed on at least one of the insert or the activating member, the attachment mechanism being configured to releasably retain the insert and the activating member in operable communication.

16. The oral device of claim 15, wherein the attachment mechanism comprises a protrusion extending from the insert or the activating member and a receptacle on the other of the insert or the activating member configured to releasably receive the protrusion.

17. The oral device of claim 11, wherein the activating member comprises a light source.

18. The oral device of claim 17, wherein at least a portion of the facial portion is chosen to allow for at least 80% transmission of light emitted from the light source.

19. A kit comprising:
an activating member comprising:
a housing configured for placement in an oral cavity, the housing having a receptacle, and
a power source disposed in the housing;
a first insert configured for removable attachment to the housing, the first insert comprising:
a first facial portion comprising a first surface configured for placement proximate a facial surface of teeth within the oral cavity,
a first lingual portion comprising a second surface spaced from the first surface and configured for placement proximate a lingual surface of the teeth, and
a first base connecting the first facial portion and the first lingual portion, the first base, the first surface, and the second surface forming a first channel for receiving the teeth; and
a second insert configured for removable attachment to the housing, the second insert comprising:
a second facial portion comprising a third surface configured for placement proximate the facial surface of the teeth,
a second lingual portion comprising a fourth surface spaced from the third surface and configured for placement proximate a lingual surface of the teeth, and
a second base connecting the second facial portion and the second lingual portion, the second base, the third surface, and the fourth surface forming a second channel for receiving the teeth, wherein the first insert further comprises a first active agent disposed in the first channel and the second insert further comprises a second active agent disposed in the second channel;

wherein one of the first or second inserts comprises a first electrical contact disposed on an external surface of the first or second insert;

wherein the activating member comprises a second electrical contact on an interior surface of the receptacle; and wherein positioning of one of the first or second inserts in the receptacle places the first electrical contact in contact with the second electrical contact.

* * * * *